United States Patent [19]

Kawai

[11] 4,447,208
[45] May 8, 1984

[54] DENTAL POLISHER

[75] Inventor: Masakatsu Kawai, Kashihara, Japan

[73] Assignee: Shofu, Inc., Kyoto, Japan

[21] Appl. No.: 483,839

[22] Filed: Apr. 11, 1983

[30] Foreign Application Priority Data

Apr. 23, 1982 [JP] Japan ................... 57-68964

[51] Int. Cl.³ ............................................. A61C 3/06
[52] U.S. Cl. ............................................... 433/166
[58] Field of Search ................. 433/166; 51/328, 358, 51/401

[56] References Cited

U.S. PATENT DOCUMENTS 3,858,368 1/1975 Cochereu ..................... 433/166
4,055,897 11/1977 Beix ............................... 433/166

Primary Examiner—Robert Peshock
Attorney, Agent, or Firm—Eugene E. Geoffrey, Jr.

[57] ABSTRACT

An improved dental polishing tool, which is attached to a rotating mandrel and used for polishing a tooth or teeth, and which is soft and resilient and can polish the tooth or teeth readily and safely without injuring gingiva and mucous membrane.

6 Claims, 6 Drawing Figures

DENTAL POLISHER

This invention relates to an improved dental polisher and a method of making same. The dental polisher is a tool which is attached to a rotating mandrel of a dental engine and used for polishing or finishing a surface of a tooth or various prosthetic or restorative materials.

There are many types of dental polishers, such as disc-type, cannon ball-type, cup-shaped and so on. Resiliently flexible types are also known in the art, as described in the article of G. Goto et al entitled: "Study of Surface Finishing of Composite Restorative Materials II, Finishing with Quasite Disc", SHIKAGAKUHO (Dental Review of Japan), Vol. 79, No. 3 (1979), pp. 581–585. Such prior art dental polishers are formed of a mixture of a base material such as rubber or synthetic resin and an abrasive material such as zirconium flour or alumina particles. However, dental polishers of this type are relatively low in polishing efficiency or polishing power due to the relatively low abrasive density in the surface, since this density is determined by the abrasive concentration of the mixture, which is limited by desired physical properties of the product, such as elasticity and hardness.

Therefore, an object of this invention is to provide an improved dental polisher having a desired flexibility and hardness and improved polishing power.

Another object of this invention is to provide a novel method of making improved dental polishers.

According to this invention, a dental polisher is provided comprising a flexible core formed of rubber or resilient synthetic resin and a surface coating including abrasive particles.

These and other features and objects of this invention will be described in more detail hereinunder with reference to the accompanying drawings.

IN THE DRAWINGS

Figure 1A:
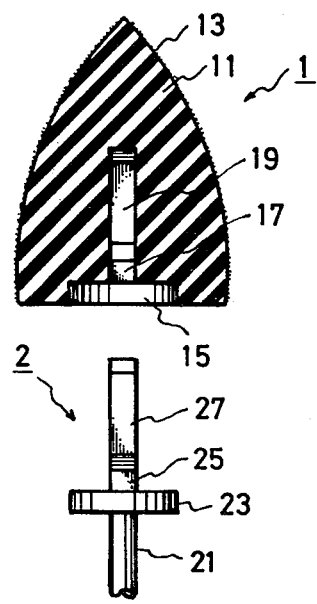
FIGS. 1a and 1b are cross sectional front and side views, respectively, of an embodiment of the dental polisher according to this invention.
Figure 1B:
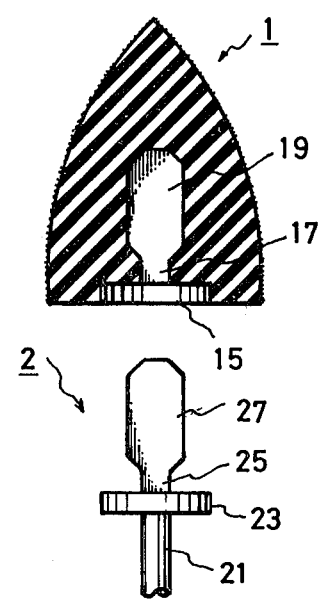

Referring to FIGS. 1a and 1b, there is shown an embodiment of a dental polisher according to this invention, which consists of a cannon ball-type flexible body 1 and a rotating shaft 2. The body 1 includes a resilient core 11 formed of soft rubber in a cannon ball shape and an abrasive coating 13 which will be described in detail later. Along the axis of the core 11, there is formed an inner cavity consisting of a flat circular depression 15, a relatively narrow neck portion 17 and an enlarged flat portion 19.

The rotating shaft 2 consists of a round rod portion 21, a circular disc portion 23, a relatively narrow neck portion 25 and an enlarged flat, head portion 27. The portions 23, 25 and 27 correspond relatively to the portions 15, 17 and 19 of the inner cavity of the core 11 and have substantially the same contours and dimensions as the latter. Accordingly, when the head portion 27 is forced into the inner cavity of the core 11, it passes the neck portion 17 due to its elasticity and is trapped in the indent of the portion 19 and the disc portion 23 fits in the depression 15, thereby providing a fixation of both members against the axial and rotational movement.

Figure 2:
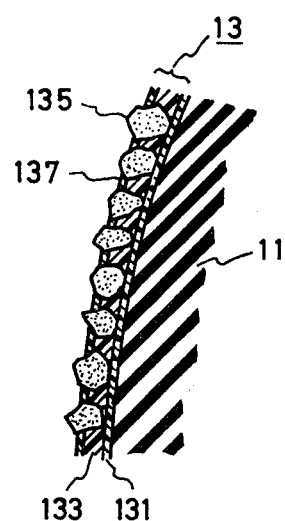
FIG. 2 is an enlarged cross sectional view of a part of the embodiment of FIG. 1 illustrating the surface coating formed in accordance with the method of this invention.

The surface of the core 11 of the body 1, carries an abrasive coating 13 as shown in the enlarged view of FIG. 2. In forming the coating 13, a thin polyurethane adhesive layer 131 is first deposited on the surface of the core 11 and dried and, then, an epoxy adhesive layer 133 is coated thereon. Abrasive particles such as white alundum No. 1,000 denoted by the numeral 135 are scattered uniformly on the unhardened adhesive layer 133 and the structure is heated at 100° C. for 30 minutes to cure the adhesive. Finally, a thin layer 137 of dilute epoxy adhesive is deposited and, then, heated at 100° C. for one hour to completely cure the adhesive layers 133 and 137.

According to this method, the abrasive particles can be distributed at much higher density over the surface of the core 11 as compared with that which could be realized in the prior art. Moreover, as seen from FIG. 2, the rubber matrix which is relatively resistant to abrasion is not exposed to the surface and, therefore, does not directly contact the object to be polished. These factors are the principal reasons why the inventive polisher exhibits a highly improved polishing power over the prior art structures.

The coupling between the body 1 and the shaft 2 is not limited to the indent type as shown. It is also useful to embed a female threaded member in the core 11 and provide the shaft end with a male screw.

Figure 3:
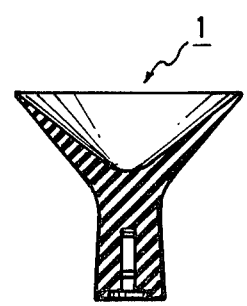
FIG. 3 is a cross sectional view representing another embodiment of this invention.
Figure 4:
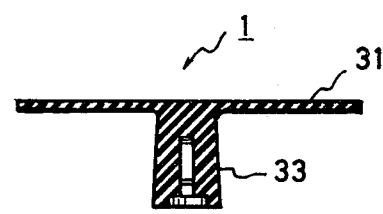
FIG. 4 is a cross sectional view representing a further embodiment of this invention.
Figure 5:
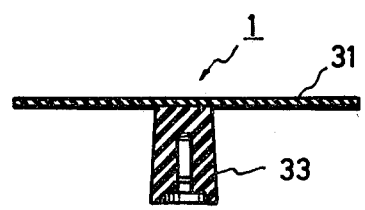
FIG. 5 is a cross sectional view representing a modification of the embodiment of FIG. 4.

The contour of the body 1 can be modified also as occasion demands. FIGS. 3 and 4 show two modified contours of the body in the form of cup and disc types, respectively. FIG. 5 is a modification of the body 1 of FIG. 4. In this modification (FIG. 5), the disc portion 31 and the boss portion 33 of the body 1 are prepared separately, while those of FIG. 4 are formed integrally. In FIG. 5, the disc 31 is punched from a rubber sheet previously provided with an abrasive coating which is the same as the coating 13 of FIG. 2, and then coupled to the boss 33 with adhesive. Therefore, the body 1 of FIG. 5 is simpler and less costly in manufacture than that of FIG. 4.

Though, in the above description, the core 11 of the body 1 has been shown as made of rubber, it may be made of any suitable material, such as synthetic resin, having physical and mechanical characteristics similar to those of rubber.

What is claimed is:

1. A dental polisher, comprising a resilient, flexible body made of rubber or synthetic resin, and a rotating shaft coupled to said body, said body having a first polyurethane layer deposited on the surface of said body, a second epoxy adhesive layer deposited on said first layer, abrasive particles scattered on said second layer and a third adhesive layer deposited on said second layer and over said abrasive particles.

2. A dental polisher, according to claim 1, wherein said body and said shaft are coupled detachably.

3. A dental polisher, according to claim 1, wherein said body is composed of a flat disc portion and a central boss portion coupled to said shaft, and said disc portion is secured to said boss portion through an adhesive agent.

4. A dental polisher, according to claim 2, wherein said body is composed of a flat disc portion and a central boss portion coupled to said shaft, and said disc portion is secured to said boss portion through an adhesive agent.

5. A dental polisher according to claim 1 wherein said third adhesive layer is a dilute epoxy resin.

6. A dental polisher according to claim 5 wherein said abrasive particles are alundum containing principally aluminum oxide.